United States Patent
Ikuma (10) Patent No.: US 11,964,089 B2
(45) Date of Patent: Apr. 23, 2024

(54) BLOOD PURIFICATION APPARATUS AND METHOD OF TRAPPING BUBBLES THEREIN

(71) Applicant: Nikkiso Company Limited, Tokyo (JP)

(72) Inventor: Shingo Ikuma, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 828 days.

(21) Appl. No.: 17/022,633

(22) Filed: Sep. 16, 2020

(65) Prior Publication Data

US 2020/0405941 A1    Dec. 31, 2020

Related U.S. Application Data

(63) Continuation of application No. PCT/JP2019/012610, filed on Mar. 25, 2019.

(30) Foreign Application Priority Data

Mar. 26, 2018   (JP) ............................... 2018-057841

(51) Int. Cl.
    *A61M 1/36*      (2006.01)
    *A61M 1/16*      (2006.01)

(52) U.S. Cl.
    CPC ........ *A61M 1/3626* (2013.01); *A61M 1/1647* (2014.02); *A61M 1/3629* (2014.02); *A61M 1/3638* (2014.02); *A61M 1/3663* (2013.01)

(58) Field of Classification Search
    CPC .............. A61M 1/3629; A61M 1/1647; A61M 1/3638; A61M 1/3663; A61M 1/3465;
    (Continued)

(56) References Cited

U.S. PATENT DOCUMENTS 4,966,691 A * 10/1990 Brous ................. A61M 1/1605
                                                        210/87
5,437,634 A *  8/1995 Amano ............... A61M 1/3644
                                                        604/65
(Continued)

FOREIGN PATENT DOCUMENTS

EP      2745860 A1 *  6/2014  .............. A61M 1/14
EP      3069742 A1    9/2016
(Continued)

OTHER PUBLICATIONS

Extended European Search Report of the European Patent Office in 19775561.4, dated Nov. 29, 2021, 14 pgs.

*Primary Examiner* — Susan S Su
*Assistant Examiner* — Eric Rassavong
(74) *Attorney, Agent, or Firm* — Young Basile Hanlon & MacFarlane, P.C.

(57) ABSTRACT

A blood purification apparatus that includes a blood circuit including an arterial blood circuit and a venous blood circuit and having a flow route that allows a patient's blood to extracorporeally circulate from a distal end of the arterial blood circuit to a distal end of the venous blood circuit; a blood purifier connected to a proximal end of the arterial blood circuit and to a proximal end of the venous blood circuit and that purifies the blood flowing through the blood circuit; an air-trap chamber connected to the blood circuit and that traps bubbles contained in liquid flowing in the flow route of the blood circuit; and a blood pump provided to the arterial blood circuit and being capable of delivering the liquid within the blood circuit. An upstream bubble-detecting unit attached to a position of the blood circuit on an upstream side with respect to the air-trap chamber and that detects bubbles contained in the liquid flowing in the blood circuit; and a control unit that reduces, at the detection of any (Continued)

bubbles by the upstream bubble-detecting unit, a flow rate of the liquid flowing into the air-trap chamber.

14 Claims, 10 Drawing Sheets

(58) Field of Classification Search
 CPC ........ A61M 1/3649; A61M 2205/3334; A61M 1/3627
 See application file for complete search history.

(56) References Cited

U.S. PATENT DOCUMENTS

| | | | |
|---|---|---|---|
| 2004/0184953 A1* | 9/2004 | Litzie | A61M 60/113 604/6.14 |
| 2008/0098798 A1* | 5/2008 | Riley | A61M 5/365 73/19.03 |
| 2009/0101550 A1* | 4/2009 | Muller | A61M 1/34 210/87 |
| 2010/0191164 A1 | 7/2010 | Sasaki et al. | |
| 2011/0132838 A1* | 6/2011 | Curtis | A61M 1/1647 210/133 |
| 2014/0166579 A1 | 6/2014 | Gagel et al. | |
| 2014/0291243 A1* | 10/2014 | Curtis | A61M 1/1647 210/646 |
| 2016/0339162 A1* | 11/2016 | Curtis | G05D 7/0676 |
| 2017/0232173 A1 | 8/2017 | Perry et al. | |

FOREIGN PATENT DOCUMENTS

| | | | |
|---|---|---|---|
| JP | H10-258120 A | 9/1998 | |
| JP | 2012-192099 A | 10/2012 | |
| JP | 2016-002088 A | 1/2016 | |
| WO | 2004/082467 A2 | 9/2004 | |
| WO | 2006/047147 A1 | 5/2006 | |
| WO | WO-2006101448 A1 * | 9/2006 | .......... A61M 1/3626 |
| WO | WO-2008125893 A1 * | 10/2008 | .......... A61M 1/1627 |
| WO | 2009/132816 A1 | 11/2009 | |
| WO | 2010/030589 A2 | 3/2010 | |
| WO | 2013/031965 A1 | 3/2013 | |

* cited by examiner

(S1) · Extracorporeal circulation of blood
     · Blood purification treatment (S2) Are any bubbles detected?

(S3) Low-speed driving of blood pump

(S4) Has predetermined time elapsed?

(S5) Normal driving of blood pump (S6) Has treatment ended?

[ Fig. 3 ]

|  |  | Inside diameter of tube [mm] | | |
| --- | --- | --- | --- | --- |
|  |  | 3.4 | 4.0 | 4.7 |
| Blood flow rate [mL/min] | 600 | 275 | 199 | 144 |
|  | 500 | 239 | 172 | 125 |
|  | 400 | 202 | 146 | 106 |
|  | 300 | 165 | 119 | 86 |
|  | 200 | 128 | 93 | 67 |
|  | 100 | 92 | 66 | 48 |

(S1) · Extracorporeal circulation of blood
     · Blood purification treatment

(S2) Are any bubbles detected?

(S3) Activate narrowing unit

(S4) Has predetermined time elapsed?

(S5) Stop narrowing unit

(S6) Has treatment ended?

BLOOD PURIFICATION APPARATUS AND METHOD OF TRAPPING BUBBLES THEREIN

CROSS-REFERENCE TO RELATED APPLICATION(S)

This application is a continuation of International Application No. PCT/JP2019/012610, filed on Mar. 25, 2019, which claims priority to Japanese Application No. 2018-057841, filed on Mar. 26, 2018, the entire disclosures of which are hereby incorporated by reference.

FIELD

The present invention relates to a blood purification apparatus for purifying a patient's blood while causing the blood to extracorporeally circulate in dialysis treatment or the like performed with a dialyzer, and also relates to a method of trapping bubbles therein.

BACKGROUND

In general, dialysis treatment is performed by using a blood circuit for allowing blood collected from a patient to extracorporeally circulate and return into the patient's body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. Extracorporeal circulation of blood in the dialysis treatment is performed while the patient is being punctured with the puncture needles.

In particular, the arterial blood circuit includes a squeezable tube and a peristaltic blood pump. The blood pump is capable of delivering liquid by squeezing the squeezable tube with rollers. When the blood pump is activated, the patient's blood can be caused to extracorporeally circulate through the blood circuit. Accordingly, the blood in extracorporeal circulation undergoes blood purification treatment in the dialyzer.

Typically, the arterial blood circuit and the venous blood circuit each include an air-trap chamber for trapping bubbles contained in liquid (such as blood, a priming solution, or a substitution solution) flowing in the blood circuit. As the liquid flows through the air-trap chamber, a liquid pool (a liquid layer) is formed on the lower side of the chamber, while an air layer is formed on the upper side of the chamber. Bubbles contained in the liquid flowing therethrough move from the liquid layer to the air layer with their buoyancy. Thus, the bubbles can be trapped (see PTL 1, for example). PTL 1: Japanese Unexamined Patent Application Publication No. 2016-2088, the contents of which are expressly incorporated by reference herein.

SUMMARY

In the above known blood purification apparatus, however, if the bubbles in the liquid flowing in the blood circuit are small, the buoyancy that moves the bubbles from the liquid layer to the air layer may be insufficient. Consequently, such bubbles may flow toward the downstream side without being trapped. Therefore, to trap bubbles having relatively low buoyancy, the air-trap chamber needs to have a large capacity. In such a case, however, the volume of blood to be collected for extracorporeal circulation (the priming volume) increases. As an alternative method for assuredly trapping bubbles including relatively small ones, the flow rate of the liquid may be reduced by reducing the driving speed of the blood pump throughout the entire process of the blood purification treatment. However, such a method lowers the efficiency of treatment.

The present teachings have been conceived in view of the above circumstances and provides a blood purification apparatus including an air-trap chamber that has a reduced capacity but is capable of assuredly trapping bubbles including relatively small ones while suppressing the reduction in treatment efficiency, and also provides a method of trapping bubbles therein.

Variation 1 comprises a blood purification apparatus that includes a blood circuit including an arterial blood circuit and a venous blood circuit and having a flow route that allows a patient's blood to extracorporeally circulate from a distal end of the arterial blood circuit to a distal end of the venous blood circuit; a blood purifier connected to a proximal end of the arterial blood circuit and to a proximal end of the venous blood circuit and that purifies the blood flowing through the blood circuit; an air-trap chamber connected to the blood circuit and that traps bubbles contained in liquid flowing in the flow route of the blood circuit; and a blood pump provided to the arterial blood circuit and being capable of delivering the liquid within the blood circuit. The blood purification apparatus includes an upstream bubble-detecting unit attached to a position of the blood circuit on an upstream side with respect to the air-trap chamber and that detects bubbles contained in the liquid flowing in the blood circuit; and a control unit that reduces, at the detection of any bubbles by the upstream bubble-detecting unit, a flow rate of the liquid flowing into the air-trap chamber.

Variation 2 comprises may comprise the blood purification apparatus according to Variation 1, the control unit reduces the flow rate of the liquid flowing into the air-trap chamber by reducing a driving speed of the blood pump at the detection of any bubbles by the upstream bubble-detecting unit.

Variation 3 may comprise the blood purification apparatus according to Variation 2 further includes a substitution pump capable of performing substitution or priming by introducing dialysate into the blood circuit. Furthermore, the control unit reduces driving speeds of the blood pump and the substitution pump at the detection of any bubbles by the upstream bubble-detecting unit.

Variation 4 may comprise the blood purification apparatus according to Variation 1 further includes a narrowing unit provided at a position of the blood circuit between the air-trap chamber and the upstream bubble-detecting unit and that is capable of reducing the flow rate of the liquid by narrowing the flow route of the blood circuit. Furthermore, the control unit reduces, at the detection of any bubbles by the upstream bubble-detecting unit, the flow rate of the liquid flowing into the air-trap chamber by activating the narrowing unit to narrow the flow route.

Variation 5 may comprise the blood purification apparatus according to any of Variations 1 to 4, the control unit resets the flow rate of the liquid flowing into the air-trap chamber to a preset flow rate at an elapse of a predetermined time period after reducing the flow rate of the liquid.

Variation 6 may comprise a method of trapping bubbles in a blood purification apparatus, the apparatus including a blood circuit including an arterial blood circuit and a venous blood circuit and having a flow route that allows a patient's blood to extracorporeally circulate from a distal end of the arterial blood circuit to a distal end of the venous blood circuit; a blood purifier connected to a proximal end of the arterial blood circuit and to a proximal end of the venous blood circuit and that purifies the blood flowing through the blood circuit; an air-trap chamber connected to the blood circuit and that traps bubbles contained in liquid flowing in the flow route of the blood circuit; and a blood pump provided to the arterial blood circuit and being capable of delivering the liquid within the blood circuit. The blood purification apparatus further includes an upstream bubble-detecting unit attached to a position of the blood circuit on an upstream side with respect to the air-trap chamber and that detects bubbles contained in the liquid flowing in the blood circuit. Furthermore, a flow rate of the liquid flowing into the air-trap chamber is reduced at the detection of any bubbles by an upstream bubble-detecting unit.

Variation 7 may comprise the method of trapping bubbles in the blood purification apparatus according to Variation 6, the flow rate of the liquid flowing into the air-trap chamber is reduced by reducing a driving speed of the blood pump at the detection of any bubbles by the upstream bubble-detecting unit.

Variation 8 may comprise the method of trapping bubbles in the blood purification apparatus according to Variation 7, the blood purification apparatus further includes a substitution pump capable of performing substitution or priming by introducing dialysate into the blood circuit. Furthermore, driving speeds of the blood pump and the substitution pump are reduced at the detection of any bubbles by the upstream bubble-detecting unit.

Variation 9 may comprise the method of trapping bubbles in the blood purification apparatus according to Variation 6, the blood purification apparatus further includes a narrowing unit provided at a position of the blood circuit between the air-trap chamber and the upstream bubble-detecting unit and that is capable of reducing the flow rate of the liquid by narrowing the flow route of the blood circuit. Furthermore, at the detection of any bubbles by the upstream bubble-detecting unit, the flow rate of the liquid flowing into the air-trap chamber is reduced by activating the narrowing unit to narrow the flow route.

Variation 10 may comprise the method of trapping bubbles in the blood purification apparatus according to any of Variation 6 to 9, the flow rate of the liquid flowing into the air-trap chamber is reset to a preset flow rate at an elapse of a predetermined time period after the flow rate of the liquid is reduced.

Variations 1 and 6 may comprise the blood purification apparatus includes the upstream bubble-detecting unit attached to a position of the blood circuit on the upstream side with respect to the air-trap chamber and that detects bubbles contained in the liquid flowing in the blood circuit. Furthermore, the flow rate of the liquid flowing into the air-trap chamber is reduced at the detection of any bubbles by the upstream bubble-detecting unit. Therefore, bubbles including relatively small ones can be trapped assuredly in the air-trap chamber having a reduced capacity. Furthermore, the reduction in treatment efficiency can be suppressed.

Variations 2 and 7 may comprise, the flow rate of the liquid flowing into the air-trap chamber is reduced by reducing the driving speed of the blood pump at the detection of any bubbles by the upstream bubble-detecting unit. Therefore, bubbles can be trapped assuredly by controlling the driving speed of the blood pump. Hence, no additional components are necessary.

Variations 3 and 8 may comprise the blood purification apparatus includes the substitution pump capable of performing substitution or priming by introducing the dialysate into the blood circuit. Furthermore, the driving speeds of the blood pump and the substitution pump are reduced at the detection of any bubbles by the upstream bubble-detecting unit. Therefore, bubbles can be trapped assuredly by controlling the driving speeds of the blood pump and the substitution pump. Hence, no additional components are necessary.

Variations 4 and 9 may comprise the blood purification apparatus includes the narrowing unit provided at a position of the blood circuit between the air-trap chamber and the upstream bubble-detecting unit and that is capable of reducing the flow rate of the liquid by narrowing the flow route of the blood circuit. Furthermore, the flow rate of the liquid flowing into the air-trap chamber is reduced by activating the narrowing unit to narrow the flow route at the detection of any bubbles by the upstream bubble-detecting unit. Therefore, bubbles can be trapped assuredly without changing the driving speed of the blood pump but by activating the narrowing unit.

Variations 5 and 10 comprise the preset flow rate of the liquid is resumed at the elapse of a predetermined time period after the flow rate of the liquid flowing into the air-trap chamber is reduced. Therefore, after bubbles are trapped in the air-trap chamber, the flow rate of the liquid flowing in the blood circuit can be reset automatically.

DETAILED DESCRIPTION

Embodiments of the present invention will now be described specifically with reference to the drawings.

Figure 1:
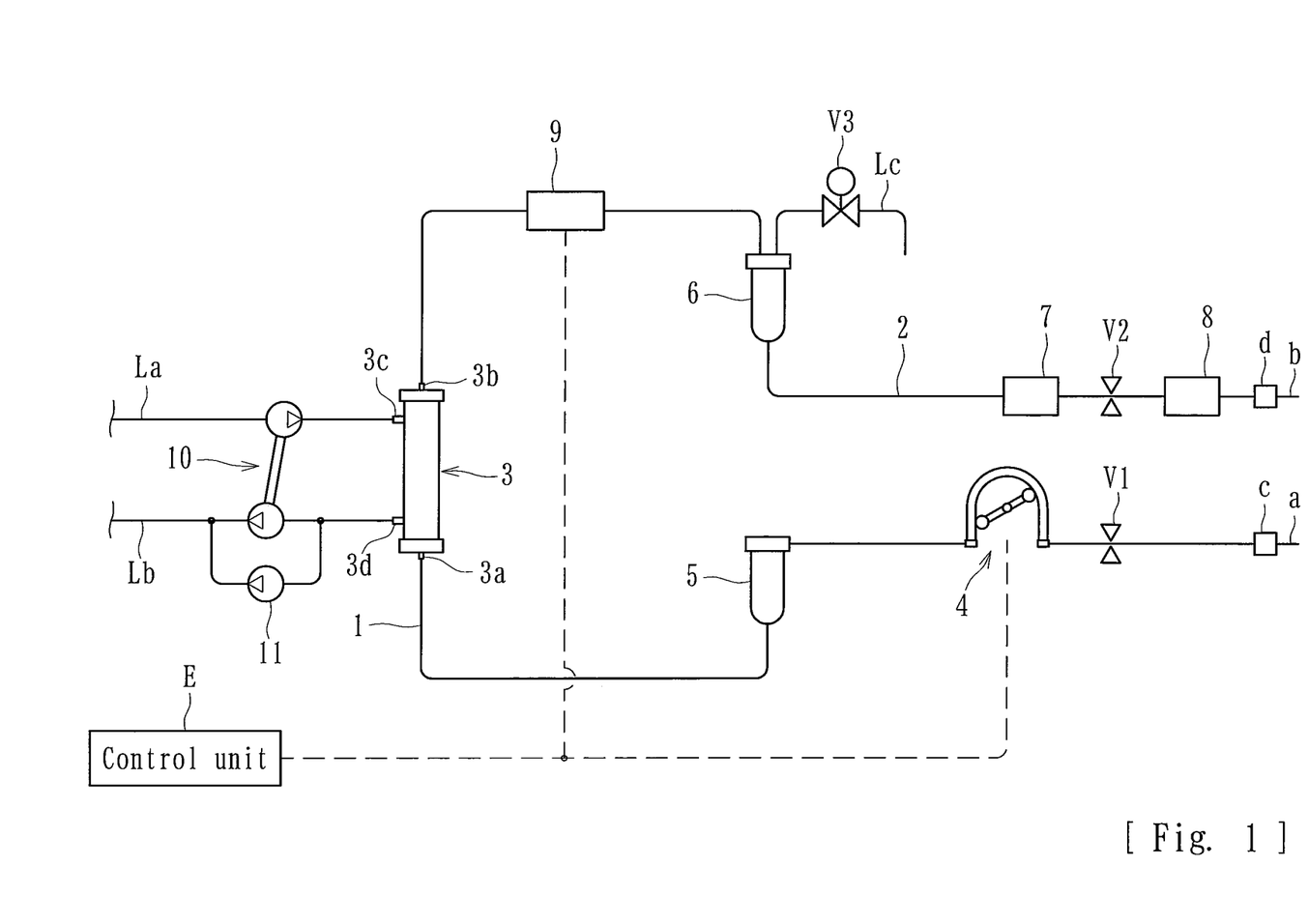
FIG. 1 is a schematic diagram of a dialysis apparatus (a blood purification apparatus) according to a first embodiment of the present invention.

A blood purification apparatus according to a first embodiment is a dialysis apparatus intended for dialysis treatment and basically includes, as illustrated in FIG. 1, a blood circuit including an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, a blood pump 4, an air-trap chamber 5 connected to the arterial blood circuit 1, an air-trap chamber 6 connected to the venous blood circuit 2, a bubble detection unit 7, a blood identifier 8, an upstream bubble-detecting unit 9, and a control unit E.

The arterial blood circuit 1 is provided with an arterial puncture needle a connected to a distal end thereof through a connector (c). The blood pump 4, which is of a peristaltic type, and the air-trap chamber 5 are provided at respective halfway positions of the arterial blood circuit 1. The venous blood circuit 2 is provided with a venous puncture needle (b) connected to a distal end thereof through a connector d. The upstream bubble-detecting unit 9 and the air-trap chamber 6 are provided at respective halfway positions of the venous blood circuit 2. Furthermore, the arterial blood circuit 1 and the venous blood circuit 2 are provided on respective distal sides thereof (near the respective connectors (c) and (d)) with respective tube clamps V1 and V2, which are capable of closing or opening respective flow routes. The tube clamps V1 and V2 may be replaced with other flow-route-closing mechanisms (such as electromagnetic valves or pinch valves).

When the blood pump 4 is activated while a patient is punctured with the arterial puncture needle a and the venous puncture needle b, the patient's blood flows through the arterial blood circuit 1 and reaches the dialyzer 3, where the blood is purified. Then, the blood flows through the venous blood circuit 2 and returns into the patient's body. That is, blood purification treatment is performed by purifying the patient's blood with the dialyzer 3 while causing the blood to extracorporeally circulate through the blood circuit from the distal end of the arterial blood circuit 1 to the distal end of the venous blood circuit 2. In this specification, the side of the puncture needle for blood removal (blood collection) is referred to as the "arterial" side, and the side of the puncture needle for blood return is referred to as the "venous" side. The "arterial" side and the "venous" side are not defined in accordance with which of the artery and the vein is to be the object of puncture.

The bubble detection unit 7 is attached to a distal portion of the venous blood circuit 2 (on a side nearer to the dialyzer 3 with respect to the tube clamp V2). The bubble detection unit 7 is a sensor capable of detecting bubbles contained in liquid flowing there. During the blood purification treatment, if any bubbles are detected by the bubble detection unit 7 while the patient's blood is extracorporeally circulating through the blood circuit, the tube clamp V2 closes the flow route, whereby the bubbles are prevented from reaching the patient's body.

The blood identifier 8 is attached to the distal portion of the venous blood circuit 2 (on a side nearer to the connector d with respect to the tube clamp V2). The blood identifier 8 is a sensor capable of identifying whether the liquid flowing there is blood. Before the blood purification treatment is started, whether blood has been substituted for a priming solution can be identified by the blood identifier 8. When the blood purification treatment is ended and before the blood in the blood circuit is returned to the patient, whether the substitution solution has been substituted for the blood can be identified by the blood identifier 8.

The blood pump 4, provided to the arterial blood circuit 1, is capable of delivering liquid, such as blood or the priming solution, within the blood circuit by squeezing a squeezable tube in the lengthwise direction. The squeezable tube is connected to the arterial blood circuit 1. Specifically, the blood pump 4 is configured to squeeze the squeezable tube in the lengthwise direction while compressing the squeezable tube in the radial direction by using a squeezing unit (rollers), thereby causing the liquid thereinside to flow in the direction of rotation of the squeezing unit (rollers).

The air-trap chamber 5 is provided between the blood pump 4 and the dialyzer 3 in the arterial blood circuit 1. As the liquid flows through the arterial blood circuit 1, a liquid layer is formed on the lower side of the air-trap chamber 5 while an air layer is formed on the upper side of the air-trap chamber 5. Thus, bubbles contained in the liquid can be trapped in the air layer for bubble removal. The air-trap chamber 6 is provided between the upstream bubble-detecting unit 9 and the bubble detection unit 7 in the venous blood circuit 2. As the liquid flows through the venous blood circuit 2, a liquid layer is formed on the lower side of the air-trap chamber 6 while an air layer is formed on the upper side of the air-trap chamber 6. Thus, bubbles contained in the liquid can be trapped in the air layer for bubble removal.

The air-trap chamber 6 according to the present embodiment is provided with an overflow line (Lc). The overflow line (Lc) extends from the top of the air-trap chamber 6 with a distal end thereof being open to the atmosphere. The overflow line (Lc) allows the liquid (the priming solution) overflowing from the air-trap chamber 6 to be discharged to the outside. The overflow line (Lc) is provided with an electromagnetic valve V3, which is capable of closing or opening a flow route of the overflow line (Lc) at an arbitrary timing.

The dialyzer 3 has, in a housing thereof, a blood inlet 3a (a blood introduction port), a blood outlet 3b (a blood delivery port), a dialysate inlet 3c (an inlet of a dialysate flow route: a dialysate introduction port), and a dialysate outlet 3d (an outlet of the dialysate flow route: a dialysate delivery port). The blood inlet 3a is connected to the proximal end of the arterial blood circuit 1. The blood outlet 3b is connected to the proximal end of the venous blood circuit 2. The dialysate inlet 3c and the dialysate outlet 3d are connected to a dialysate introduction line (La) and a dialysate drain line (Lb), respectively, extending from a dialysis-apparatus body.

The dialyzer 3 houses a plurality of hollow fibers (not illustrated). The hollow fibers form blood purification membranes for purifying the blood. The blood purification membranes in the dialyzer 3 define blood flow routes (each extending between the blood inlet 3a and the blood outlet 3b) through which the patient's blood flows and dialysate flow routes (each extending between the dialysate inlet 3c and the dialysate outlet 3d) through which dialysate flows. The hollow fibers forming the blood purification membranes each have a number of microscopic holes (pores) extending therethrough from the outer peripheral surface to the inner peripheral surface, thereby forming a hollow fiber membrane. Impurities and the like contained in the blood are allowed to permeate through the hollow fiber membranes into the dialysate.

A duplex pump 10 is provided over the dialysate introduction line (La) and the dialysate drain line (Lb) in the dialysis-apparatus body. The dialysate drain line (Lb) is provided with a bypass line that bypasses the duplex pump 10. The bypass line is provided with an ultrafiltration pump 11 for removing water from the patient's blood flowing in the dialyzer 3. One end of the dialysate introduction line La is connected to the dialyzer 3 (the dialysate inlet 3c), and the other end is connected to a dialysate supply device (not illustrated) that prepares a dialysate at a predetermined concentration. One end of the dialysate drain line Lb is connected to the dialyzer 3 (the dialysate outlet 3d), and the other end is connected to a drainage unit, not illustrated. The dialysate supplied from the dialysate supply device flows through the dialysate introduction line (La) into the dialyzer 3, and further flows through the dialysate drain line (Lb) into the drainage unit.

The present embodiment employs the upstream bubble-detecting unit 9 attached to a position of the blood circuit (the venous blood circuit 2) on the upstream side with respect to the air-trap chamber 6 and that detects bubbles contained in the liquid, such as blood, flowing in the venous blood circuit 2; and the control unit (E) that reduces the flow rate of the liquid flowing into the air-trap chamber 6 by reducing the driving speed of the blood pump 4 if any bubbles are detected by the upstream bubble-detecting unit 9.

As with the bubble detection unit 7, the upstream bubble-detecting unit 9 is a sensor capable of detecting bubbles contained in liquid and includes, for example, a pair of ultrasonic vibrators (an oscillating device and a receiving device) formed of piezoelectric devices. Specifically, the upstream bubble-detecting unit 9 (as well as the bubble detection unit 7) is capable of emitting ultrasonic waves from the ultrasonic vibrator as the oscillating device toward a flexible tube forming the blood circuit (the venous blood circuit 2), and is also capable of receiving the thus generated vibration by an ultrasonic receiver as the receiving device. The ultrasonic receiver having received the vibration generates a voltage that changes with the vibration received. The ultrasonic receiver is capable of detecting the flow of bubbles in the liquid by a fact that the detected voltage has exceeded a predetermined threshold.

Specifically, the upstream bubble-detecting unit 9 is provided at a position on the upstream side with respect to the air-trap chamber 6 (a position on the upstream side of the flow of the extracorporeally circulating blood and between the air-trap chamber 6 and the dialyzer 3). The upstream bubble-detecting unit 9 is capable of transmitting, at the detection of any bubbles, a predetermined detection signal to the control unit (E) before the bubbles reach the air-trap chamber 6. The control unit (E) is a microcomputer or the like and is electrically connected to the upstream bubble-detecting unit 9 and to the blood pump 4, thereby being capable of transmitting and receiving predetermined signals.

If the control unit (E) according to the present embodiment has identified the detection of any bubbles by receiving the predetermined detection signal from the upstream bubble-detecting unit 9, the control unit E transmits a predetermined control signal to the blood pump 4, so that the driving speed of the blood pump 4 can be reduced to a preset level. Thus, the flow rate of the blood flowing in the blood circuit can be reduced, and the flow velocity of the bubbles detected by the upstream bubble-detecting unit 9 and flowing toward the air-trap chamber 6 can be reduced. Therefore, bubbles can be trapped assuredly in the air-trap chamber 6.

At the elapse of a predetermined time period after the flow rate of the blood (liquid) flowing into the air-trap chamber 6 is reduced, the control unit (E) according to the present embodiment resets the driving speed of the blood pump 4 to an initial driving speed, so that a preset flow rate of the blood (liquid) (a normal flow rate that is set before or during the blood purification treatment) is resumed. Thus, after bubbles are trapped in the air-trap chamber 6 with the elapse of the predetermined time period, the preset flow rate can be resumed automatically.

Figure 10:
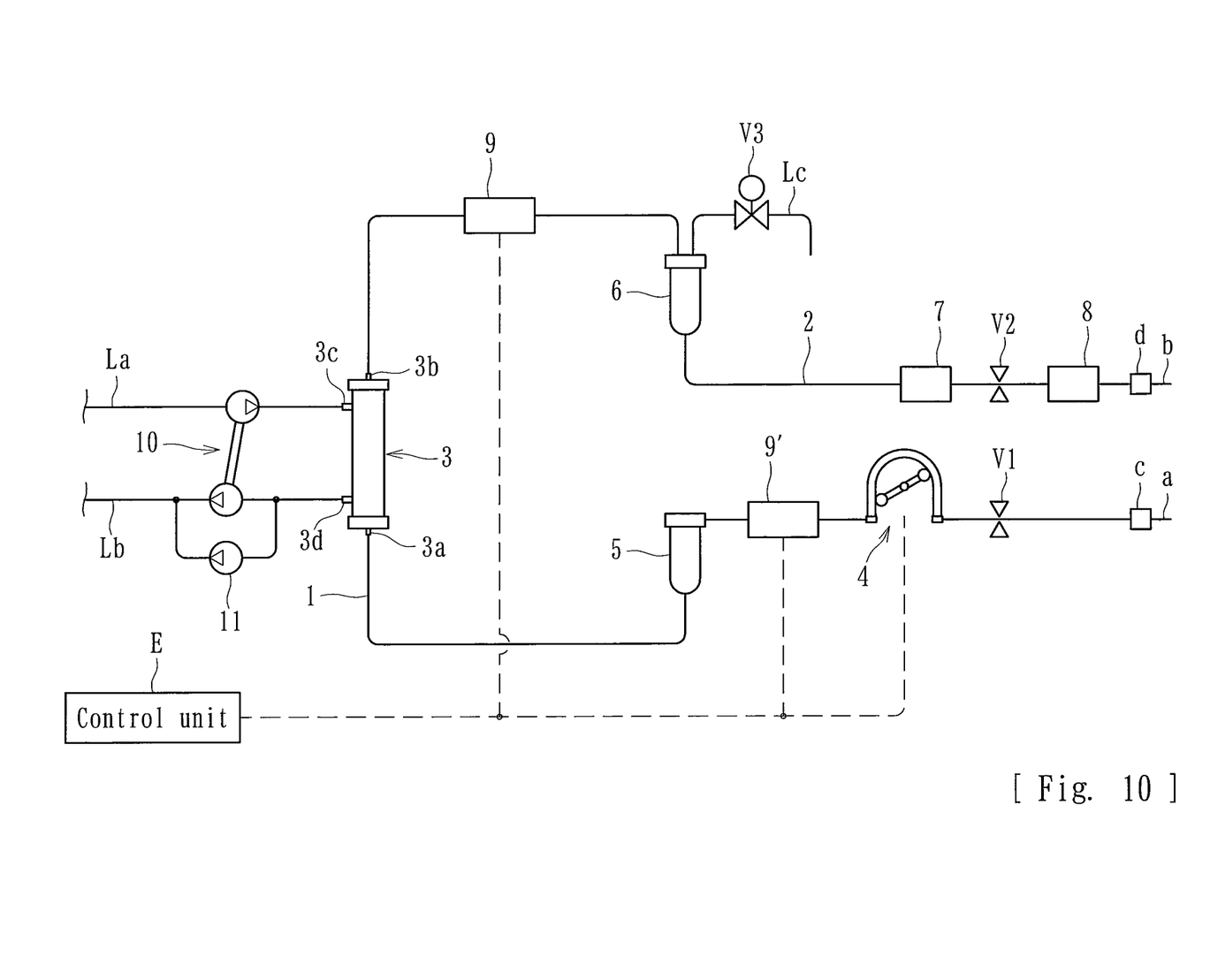
FIG. 10 is a schematic diagram of a dialysis apparatus (a blood purification apparatus) according to yet another embodiment of the present invention.

In the present embodiment, the upstream bubble-detecting unit 9 is provided on the upstream side with respect to the air-trap chamber 6 connected to the venous blood circuit 2. However, as illustrated in FIG. 10, for example, an upstream bubble-detecting unit 9' (having the same configuration and the same function as the upstream bubble-detecting unit 9) may be provided on the upstream side with respect to the air-trap chamber 5 connected to the arterial blood circuit 1 (at a position between the blood pump 4 and the air-trap chamber 5), so that the flow rate of the liquid flowing into the air-trap chamber 5 is reduced by reducing the driving speed of the blood pump 4 at the detection of any bubbles by the upstream bubble-detecting unit 9'.

The distance between the upstream bubble-detecting unit (9, 9') and the air-trap chamber (5, 6) is calculable as follows. The length of travel of bubbles in the liquid flowing through the blood circuit is calculable in accordance with the following mathematical expression: 200×(preset blood flow rate (initial blood flow rate) of blood pump 4×time period from detection of bubbles by upstream bubble-detecting unit (9, 9') until start of low-speed driving of blood pump 4+blood flow rate after reduction of driving speed of blood pump 4×time period of low-speed driving of blood pump 4)/3π(inside diameter of tube forming blood circuit)2.

Figure 3:
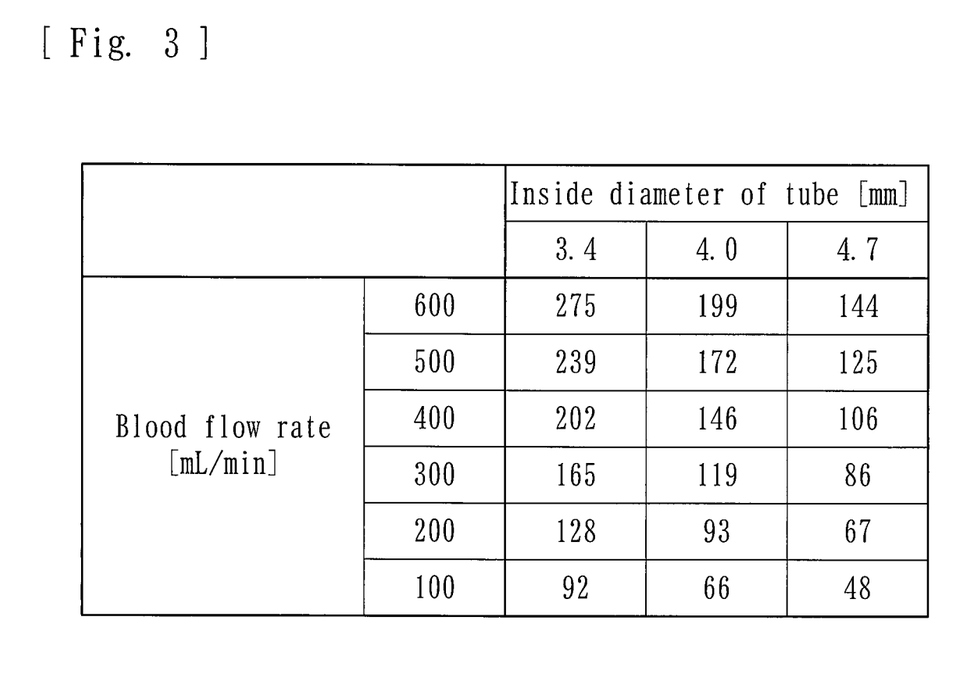
FIG. 3 is a table summarizing values of the distance between an air-trap chamber and an upstream bubble-detecting unit included in the dialysis apparatus.

Assuming that the time period from the detection of bubbles by the upstream bubble-detecting unit (9, 9') until the start of low-speed driving of the blood pump 4 is 0.2 (sec); the blood flow rate during the low-speed driving is 30 (mL/min); and the time period of the low-speed driving of the blood pump 4 is 1 (sec), a table illustrated in FIG. 3 can be obtained in accordance with the above mathematical expression. According to the table, for example, in a case where the blood circuit is formed of a tube having an inside diameter of 4.0 (mm) and the blood flow rate (the initial blood flow rate) is set to 500 (mL/min), bubbles travel by 172 (mm). Therefore, the distance between the upstream bubble-detecting unit (9, 9') and the air-trap chamber (5, 6) needs to be 172 (mm) or greater.

Figure 2:
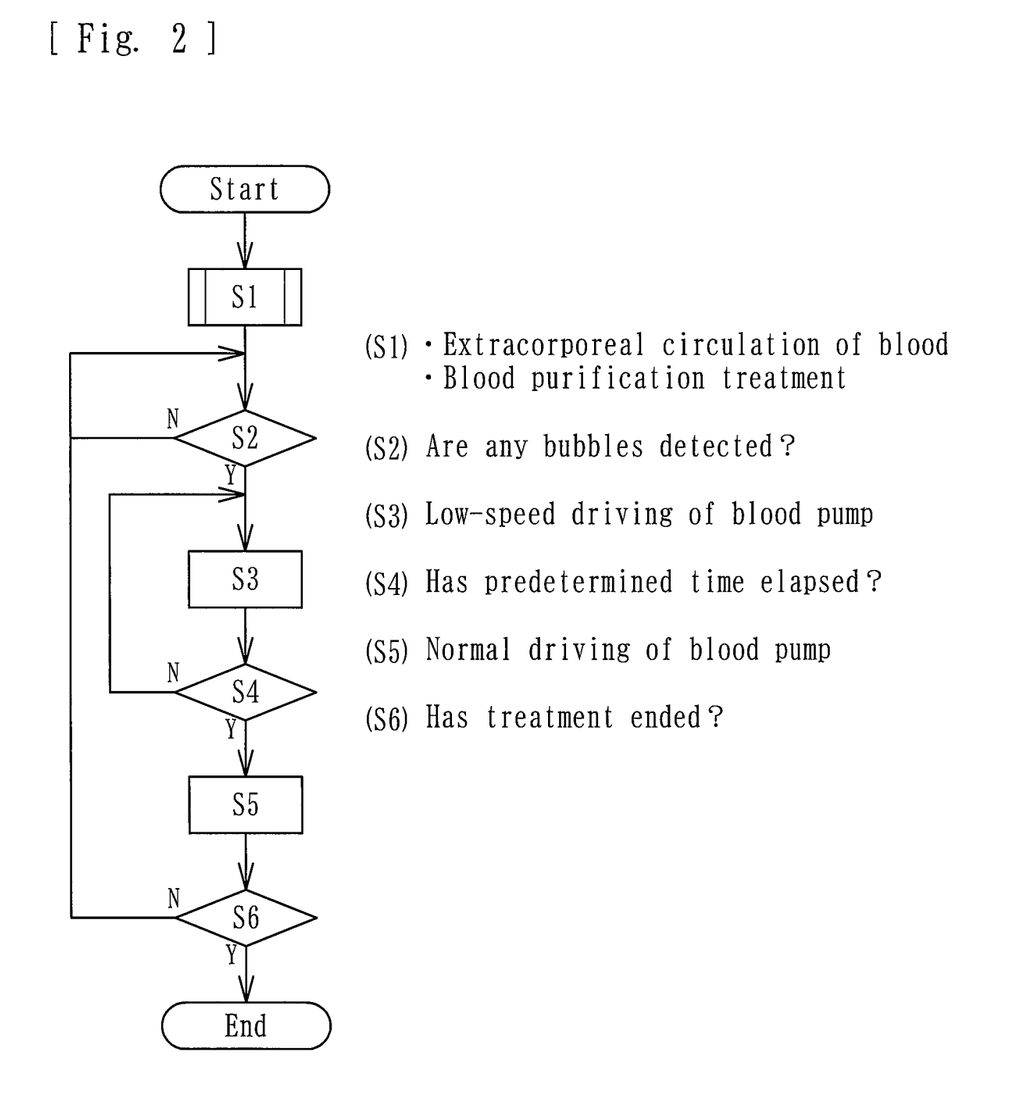
FIG. 2 is a flow chart of a control process executed by a control unit of the dialysis apparatus.

Now, a control process according to the present embodiment will be described with reference to a flow chart illustrated in FIG. 2.

First, the patient is punctured with the arterial puncture needle a and the venous puncture needle (b), and the blood pump 4 is activated, whereby blood purification treatment is started by causing the patient's blood to extracorporeally circulate through the blood circuit (S1). Then, in (S2), whether any bubbles have been detected by the upstream bubble-detecting unit 9 is checked. If it is judged that bubbles have been detected, the process proceeds to (S3), where the low-speed driving of the blood pump 4 is started (the driving speed is reduced to a level lower than the initial driving speed), whereby the flow rate of the blood flowing into the air-trap chamber 6 is reduced.

Subsequently, whether a predetermined time period has elapsed is checked (S4). If it is judged that the predetermined time period has elapsed, the process proceeds to (S5), where the normal driving (the initial driving speed) of the blood pump 4 is resumed. Then, whether the blood purification treatment has ended is checked in (S6). If it is judged that the treatment has not ended, the process returns to (S2), where whether any bubbles have been detected is checked again, and the subsequent steps of the control process are performed. On the other hand, if it is judged in S6 that the blood purification treatment has ended, the control process is ended.

According to the present embodiment, the blood purification apparatus includes the upstream bubble-detecting unit (9, 9') attached to a position of the blood circuit on the upstream side with respect to the air-trap chamber (5, 6) and that detects bubbles contained in the liquid flowing in the blood circuit. Furthermore, the flow rate of the liquid flowing into the air-trap chamber (5, 6) is reduced at the detection of any bubbles by the upstream bubble-detecting unit (9, 9'). Therefore, bubbles including relatively small ones can be trapped assuredly in the air-trap chamber (5, 6) having a reduced capacity. Furthermore, the reduction in treatment efficiency can be suppressed more than in a case where the flow rate of the liquid is constantly low.

Furthermore, according to the present embodiment, the flow rate of the liquid flowing into the air-trap chamber (5, 6) is reduced by reducing the driving speed of the blood pump 4 at the detection of any bubbles by the upstream bubble-detecting unit (9, 9'). Therefore, bubbles can be trapped assuredly by controlling the driving speed of the blood pump 4. Hence, no additional components are necessary. Furthermore, the preset flow rate of the liquid is resumed at the elapse of a predetermined time period after the flow rate of the liquid flowing into the air-trap chamber (5, 6) is reduced. Therefore, after bubbles are trapped in the air-trap chamber, the flow rate of the liquid flowing in the blood circuit can be reset automatically.

Now, a blood purification apparatus according to a second embodiment of the present invention will be described.

Figure 4:
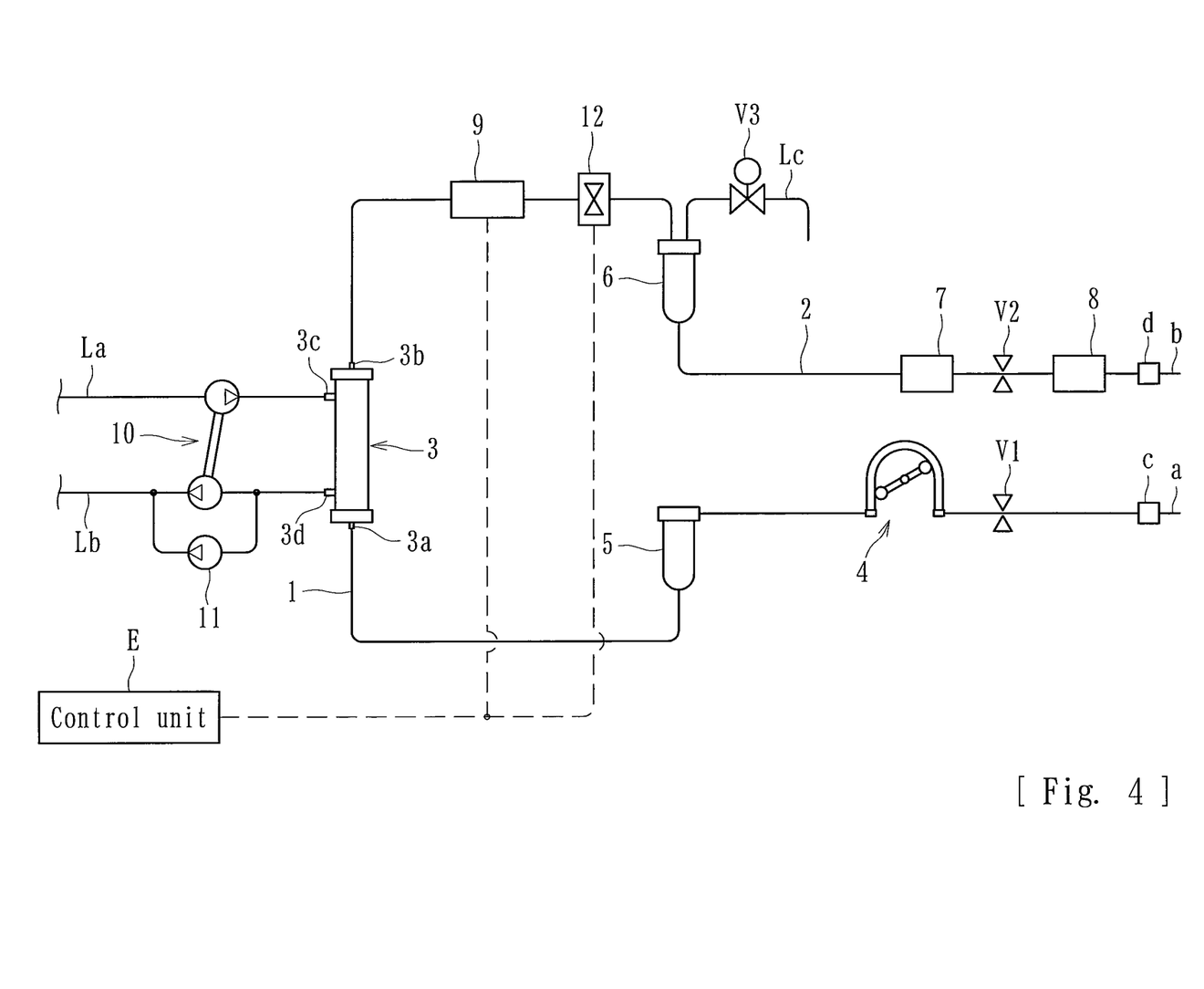
FIG. 4 is a schematic diagram of a dialysis apparatus (a blood purification apparatus) according to a second embodiment of the present invention.

As with the case of the first embodiment, the blood purification apparatus according to the present embodiment is a dialysis apparatus intended for dialysis treatment and basically includes, as illustrated in FIG. 4, a blood circuit including an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, a blood pump 4, an air-trap chamber 5 connected to the arterial blood circuit 1, an air-trap chamber 6 connected to the venous blood circuit 2, a bubble detection unit 7, a blood identifier 8, an upstream bubble-detecting unit 9, a narrowing unit 12, and a control unit (E). Elements that are the same as those described in the first embodiment are denoted by corresponding ones of the reference numerals, and detailed description of those elements is omitted.

The narrowing unit 12 is provided at a position of the blood circuit (in the present embodiment, the venous blood circuit 2) between the air-trap chamber 6 and the upstream bubble-detecting unit 9 and is capable of reducing the flow rate of the liquid by pinching and thus narrowing the flow route of the blood circuit. The narrowing unit 12 is, for example, a solenoid clamp or the like. The control unit E reduces the flow rate of the liquid flowing into the air-trap chamber 6 by activating the narrowing unit 12 to narrow the flow route at the detection of any bubbles by the upstream bubble-detecting unit 9.

Specifically, if the control unit (E) according to the present embodiment has identified the detection of any bubbles by receiving a predetermined detection signal from the upstream bubble-detecting unit 9, the control unit (E) transmits a predetermined control signal to the narrowing unit 12, so that the flow route can be narrowed. Thus, the flow rate of the blood flowing in the blood circuit can be reduced, and the flow velocity of the bubbles detected by the upstream bubble-detecting unit 9 and flowing toward the air-trap chamber 6 can be reduced. Therefore, bubbles can be trapped assuredly in the air-trap chamber 6.

Furthermore, at the elapse of a predetermined time period after the flow rate of the blood (liquid) flowing into the air-trap chamber 6 is reduced, the control unit (E) according to the present embodiment resets the flow rate of the blood (liquid), so that a preset flow rate (a normal flow rate that is set before or during the blood purification treatment) is resumed. Thus, after bubbles are trapped in the air-trap chamber 6 with the elapse of the predetermined time period, the preset flow rate can be resumed automatically.

Figure 5:
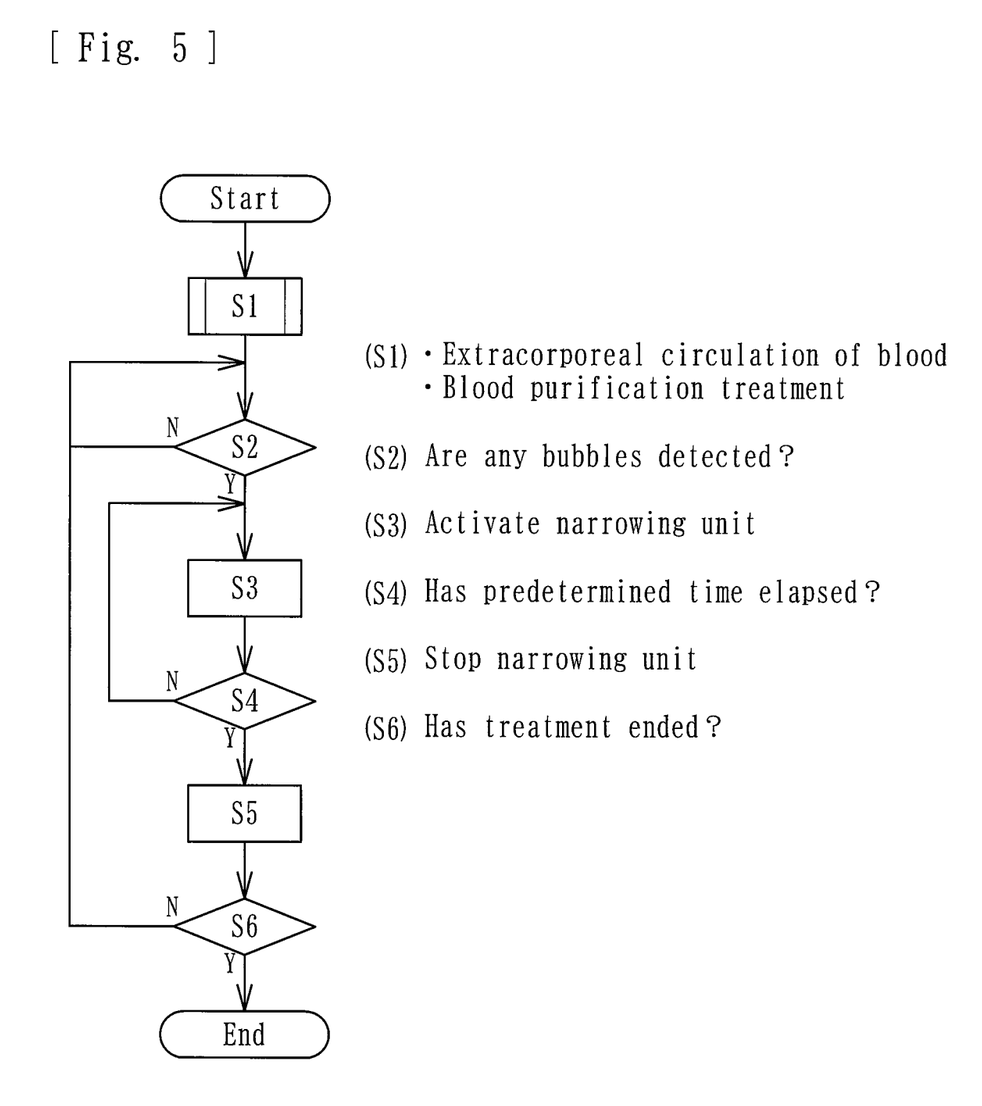
FIG. 5 is a flow chart of a control process executed by a control unit of the dialysis apparatus.

Now, a control process according to the present embodiment will be described with reference to a flow chart illustrated in FIG. 5.

First, the patient is punctured with the arterial puncture needle a and the venous puncture needle (b), and the blood pump 4 is activated, whereby blood purification treatment is started by causing the patient's blood to extracorporeally circulate through the blood circuit (S1). Then, in (S2), whether any bubbles have been detected by the upstream bubble-detecting unit 9 is checked. If it is judged that bubbles have been detected, the process proceeds to (S3), where the narrowing unit 12 is activated to reduce the flow rate of the blood flowing into the air-trap chamber 6.

Subsequently, whether a predetermined time period has elapsed is checked (S4). If it is judged that the predetermined time period has elapsed, the process proceeds to (S5), where the narrowing of the flow route by the narrowing unit 12 is disabled, and the normal blood flow rate (the initial blood flow rate) is resumed. Then, whether the blood purification treatment has ended is checked in (S6). If it is judged that the treatment has not ended, the process returns to (S2), where whether any bubbles have been detected is checked again, and the subsequent steps of the control process are performed. On the other hand, if it is judged in (S6) that the blood purification treatment has ended, the control process is ended.

According to the present embodiment, the blood purification apparatus includes the upstream bubble-detecting unit 9 attached to a position of the blood circuit on the upstream side with respect to the air-trap chamber 6 and that detects bubbles contained in the liquid flowing in the blood circuit. Furthermore, the flow rate of the liquid flowing into the air-trap chamber 6 is reduced at the detection of any bubbles by the upstream bubble-detecting unit 9. Therefore, bubbles including relatively small ones can be trapped assuredly in the air-trap chamber 6 having a reduced capacity. Furthermore, the reduction in treatment efficiency can be suppressed more than in a case where the flow rate of the liquid is constantly low.

Furthermore, according to the present embodiment, the blood purification apparatus includes the narrowing unit 12 provided at a position of the blood circuit between the air-trap chamber 6 and the upstream bubble-detecting unit 9 and that is capable of reducing the flow rate of the liquid by narrowing the flow route of the blood circuit. Furthermore, the flow rate of the liquid flowing into the air-trap chamber 6 is reduced by activating the narrowing unit 12 to narrow the flow route at the detection of any bubbles by the upstream bubble-detecting unit 9. Therefore, bubbles can be trapped assuredly without changing the driving speed of the blood pump 4 but by activating the narrowing unit 12.

Furthermore, the preset flow rate of the liquid is resumed by disabling the narrowing by the narrowing unit 12 at the elapse of a predetermined time period after the flow rate of the liquid flowing into the air-trap chamber 6 is reduced.

Therefore, after bubbles are trapped in the air-trap chamber 6, the flow rate of the liquid flowing in the blood circuit can be reset automatically. The upstream bubble-detecting unit 9 and the narrowing unit 12 according to the present embodiment are provided on the upstream side with respect to the air-trap chamber 6 connected to the venous blood circuit 2. Instead or in addition, an upstream bubble-detecting unit 9 and a narrowing unit 12 may be provided on the upstream side with respect to the air-trap chamber 5 connected to the arterial blood circuit 1.

The first and second embodiments each concern the trapping of bubbles during the blood purification treatment. The present invention is also applicable to the trapping of bubbles at the time of, for example, priming performed before the treatment. First, a case where the present invention is applied to a blood purification apparatus capable of performing pre-substitution (substitution for the blood that is yet to be purified by the dialyzer 3) will be described.

Figure 6:
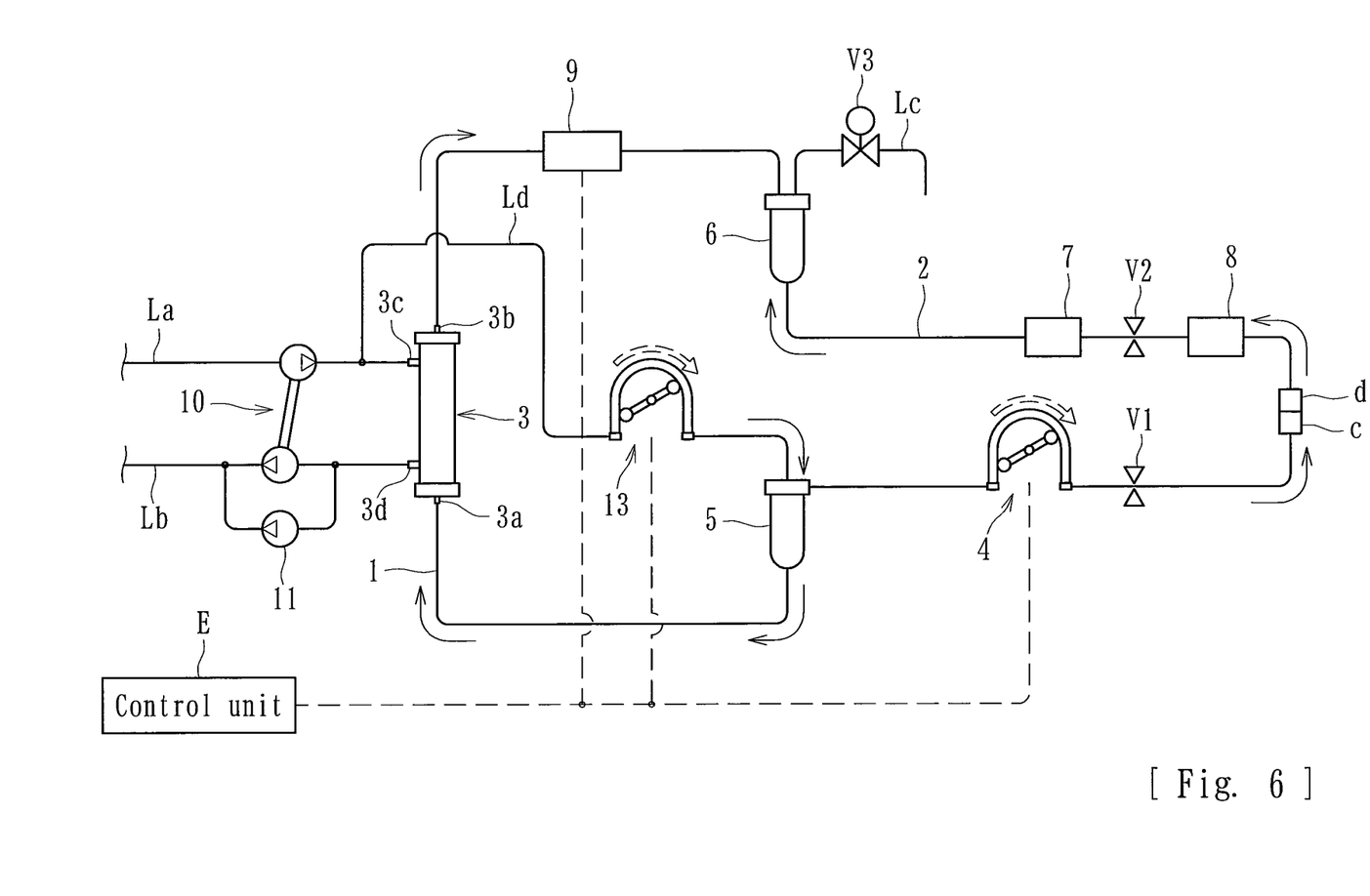
FIG. 6 is a schematic diagram of a dialysis apparatus (a blood purification apparatus intended for pre-substitution) according to another embodiment of the present invention that is in priming operation.
Figure 7:
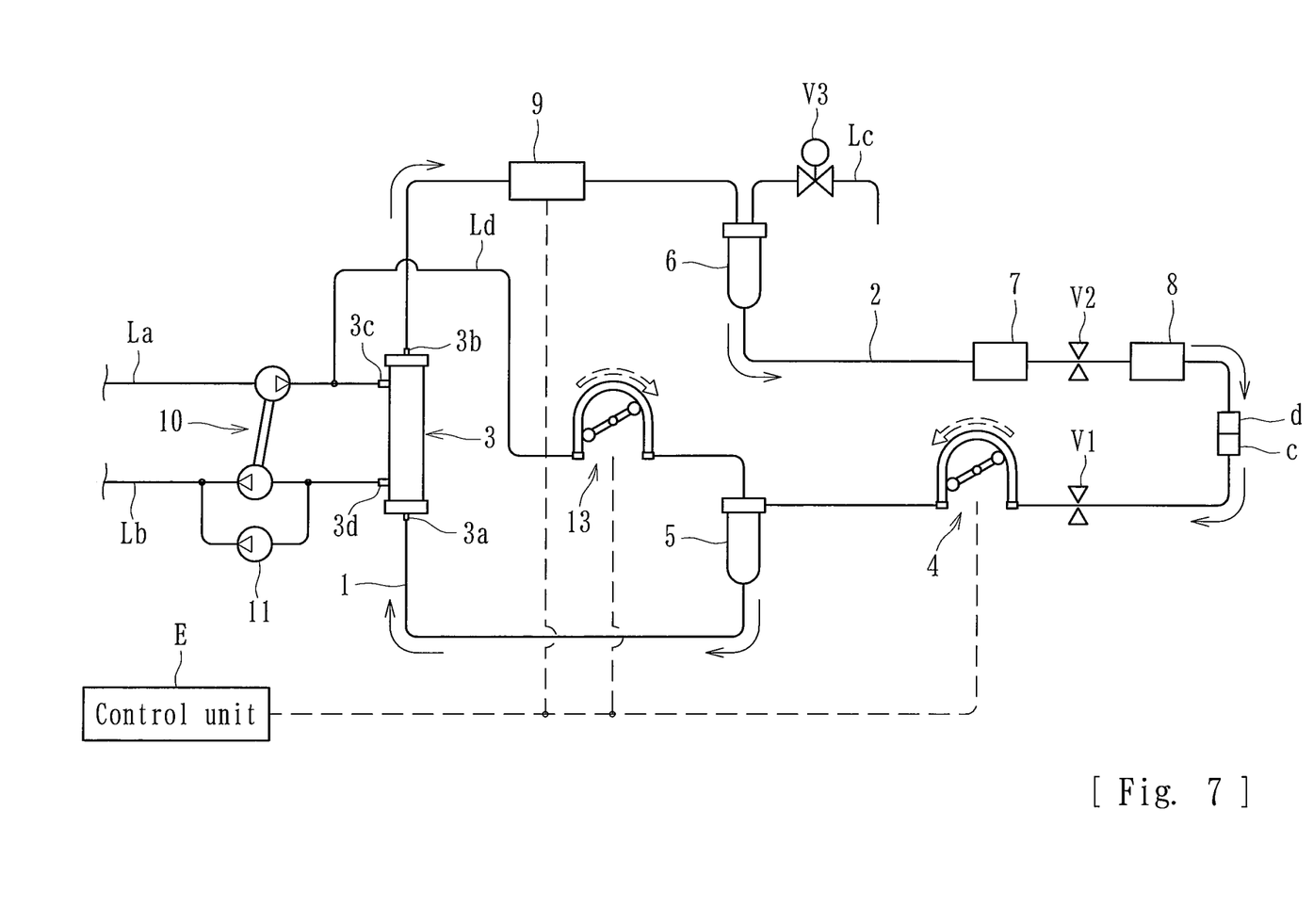
FIG. 7 is another schematic diagram of the dialysis apparatus (the blood purification apparatus intended for pre-substitution) that is in priming operation.

As illustrated in FIGS. 6 and 7, the blood purification apparatus includes a substitution line Ld connecting the dialysate introduction line La and the air-trap chamber 5 connected to the arterial blood circuit 1 to each other, so that the dialysate in the dialysate introduction line La can be introduced into the blood circuit and be used as a substitution solution and as a priming solution.

To perform priming with the above blood purification apparatus, as illustrated in FIG. 6, the connector (c) at the distal end of the arterial blood circuit 1 and the connector (d) at the distal end of the venous blood circuit 2 are connected to each other to form a closed circuit. Then, a substitution pump 13 is activated, and the blood pump 4 is rotated reversely (driven such that the liquid is delivered in the direction opposite to the direction for the blood purification treatment). Thus, some of the dialysate as the priming solution introduced into the blood circuit through the substitution line (Ld) flows toward the dialyzer 3, while the rest of the dialysate flows toward the connection between the distal end of the arterial blood circuit 1 and the distal end of the venous blood circuit 2. Then, the two flows of the dialysate merge at the air-trap chamber 6, and the merged dialysate is discharged from the overflow line (Lc). In this process, a liquid layer and an air layer are formed in the air-trap chamber 5, and bubbles and an excessive portion of the dialysate are discharged from the overflow line (Lc).

Subsequently, as illustrated in FIG. 7, while the substitution pump 13 is kept activated, the blood pump 4 is rotated normally (driven such that the liquid is delivered in the direction for the blood purification treatment). Thus, the dialysate as the priming solution introduced into the blood circuit through the substitution line (Ld) flows through the blood circuit in the direction indicated by arrows illustrated in the drawing. In this process, the control unit (E) reduces the flow rate of the priming solution (the dialysate) flowing into the air-trap chamber 6 by reducing the respective driving speeds of the blood pump 4 and the substitution pump 13 at the detection of any bubbles by the upstream bubble-detecting unit 9, so that residual bubbles can be trapped assuredly in the air-trap chamber 6.

Figure 8:
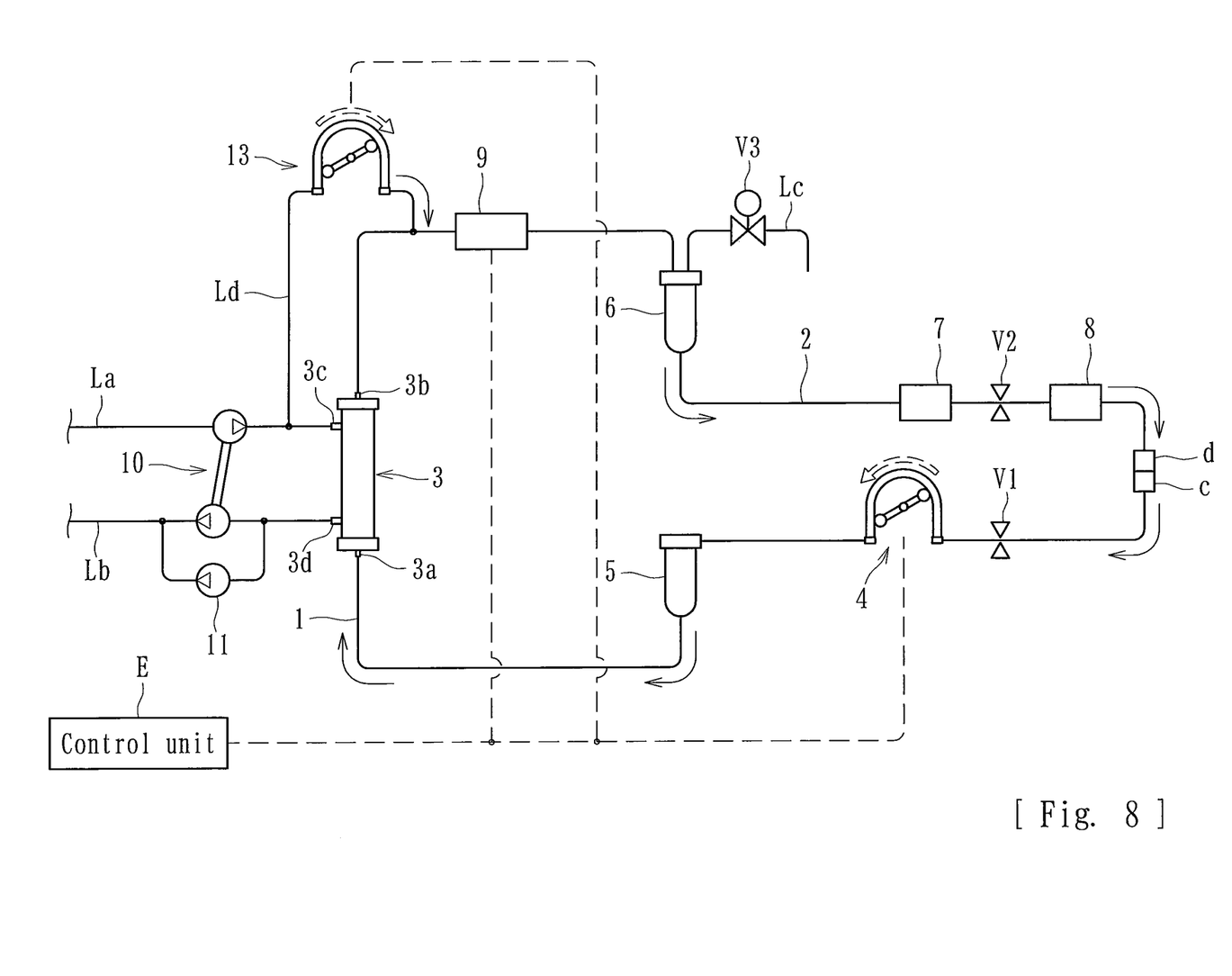
FIG. 8 is a schematic diagram of a dialysis apparatus (a blood purification apparatus intended for post-substitution) according to yet another embodiment of the present invention that is in priming operation.
Figure 9:
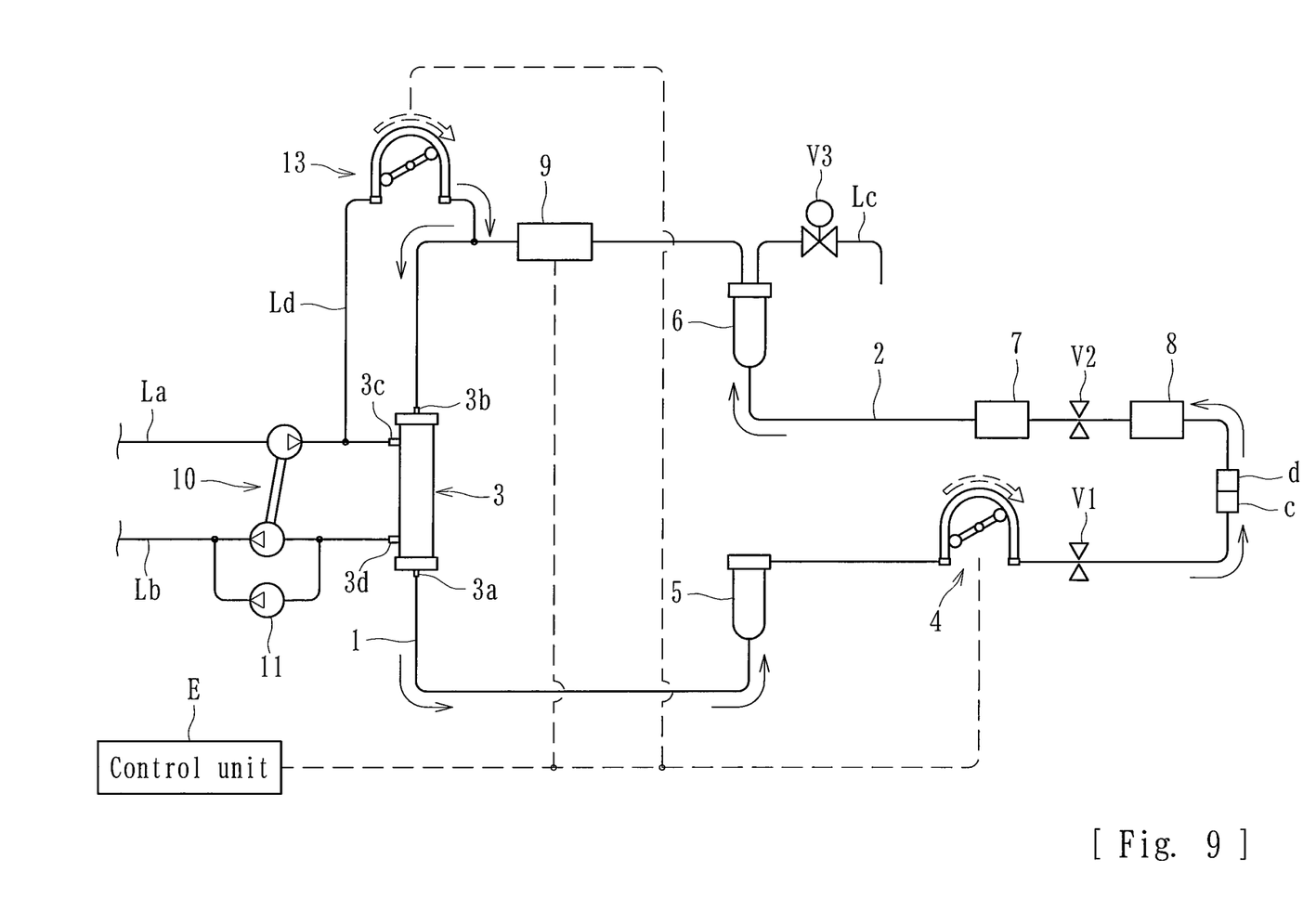
FIG. 9 is another schematic diagram of the dialysis apparatus (the blood purification apparatus intended for post-substitution) that is in priming operation.

Now, a case where the present invention is applied to a blood purification apparatus capable of performing post-substitution (substitution for the blood that has been purified by the dialyzer 3) will be described. As illustrated in FIGS. 8 and 9, the blood purification apparatus includes a substitution line (Ld) connecting the dialysate introduction line La and the venous blood circuit 2 (a position between the dialyzer 3 and the upstream bubble-detecting unit 9) to each other, so that the dialysate in the dialysate introduction line (La) can be introduced into the blood circuit and be used as a substitution solution and as a priming solution.

To perform priming with the above blood purification apparatus, as illustrated in FIG. 8, the connector (c) at the distal end of the arterial blood circuit 1 and the connector (d) at the distal end of the venous blood circuit 2 are connected to each other to form a closed circuit. Then, the substitution pump 13 is activated, and the blood pump 4 is rotated normally (driven such that the liquid is delivered in the direction for the blood purification treatment). Thus, the dialysate as the priming solution introduced into the blood circuit through the substitution line (Ld) flows through the blood circuit in the direction indicated by arrows illustrated in the drawing, and bubbles and an excessive portion of the dialysate are discharged from the overflow line (Lc).

Subsequently, as illustrated in FIG. 9, while the substitution pump 13 is kept activated, the blood pump 4 is rotated reversely (driven such that the liquid is delivered in the direction opposite to the direction for the blood purification treatment). Thus, the dialysate as the priming solution introduced into the blood circuit through the substitution line (Ld) flows through the blood circuit in the direction indicated by arrows illustrated in the drawing. In this process, the control unit (E) reduces the flow rate of the priming solution (the dialysate) flowing into the air-trap chamber 6 by reducing the respective driving speeds of the blood pump 4 and the substitution pump 13 at the detection of any bubbles by the bubble detection unit 7 (in the present embodiment, the bubble detection unit 7 corresponds to the upstream bubble-detecting unit), so that residual bubbles can be trapped assuredly in the air-trap chamber 6.

As described above, the upstream bubble-detecting unit varies with the direction in which the liquid flows through the blood circuit. If the present invention is applied to a case where the liquid (the priming solution) flows from the distal end (the connector d) of the venous blood circuit 2 toward the air-trap chamber 6 as illustrated in FIG. 9, the bubble detection unit 7 provided on the upstream side with respect to the air-trap chamber 6 serves as the upstream bubble-detecting unit according to the present invention.

The blood purification apparatus includes the substitution pump 13 capable of performing substitution or priming by introducing the dialysate into the blood circuit. Furthermore, the driving speeds of the blood pump 4 and the substitution pump 13 are reduced at the detection of any bubbles by the upstream bubble-detecting unit 9 (the bubble detection unit 7). Therefore, bubbles can be trapped assuredly by controlling the driving speeds of the blood pump 4 and the substitution pump 13. Hence, no additional components are necessary.

While some embodiments have been described above, the present invention is not limited thereto. For example, if bubbles are to be trapped in the blood purification treatment as described in the first and second embodiments, the present invention may be applied not only to a case where bubbles are trapped at the time of priming as illustrated in FIGS. 6 to 9 but also to another case (such as a blood-return process in which the blood in the blood circuit is returned to the patient after the blood purification treatment). Furthermore, the device for reducing the flow rate of the liquid flowing into the air-trap chamber (5, 6) at the detection of any bubbles by the upstream bubble-detecting unit (9, 9', 7) is not limited to the blood pump 4 and the narrowing unit 12 and may be any other device that is capable of reducing the flow rate.

Furthermore, the flow rate of the liquid flowing through the blood circuit may be reduced arbitrarily by controlling the blood pump 4 or the narrowing unit 12 in accordance with the sizes or the flow velocity of the bubbles detected by the upstream bubble-detecting unit (9, 9', 7). While the above embodiments are each applied to a dialysis apparatus intended for dialysis treatment, the present invention may also be applied to an apparatus (such as a blood purification apparatus or a plasma adsorption apparatus intended for hemodiafiltration, hemofiltration, or AFBF) that is capable of purifying a patient's blood while causing the blood to extracorporeally circulate.

The present invention is also applicable to a blood purification apparatus and a method of trapping bubbles therein in any other mode or for any other use, as long as the apparatus includes an upstream bubble-detecting unit attached to a position of a blood circuit on the upstream side with respect to an air-trap chamber and that detects bubbles contained in liquid flowing through the blood circuit; and a control unit that reduces, at the detection of any bubbles by the upstream bubble-detecting unit, the flow rate of the liquid flowing into the air-trap chamber.

REFERENCE SIGN LIST 1 arterial blood circuit
2 venous blood circuit
3 dialyzer (blood purifier)
4 blood pump
5 air-trap chamber
6 air-trap chamber
7 bubble detection unit
8 blood identifier
9, 9' upstream bubble-detecting unit
10 duplex pump
11 ultrafiltration pump
12 narrowing unit
13 substitution pump
E control unit
La dialysate introduction line
Lb dialysate drain line
Lc overflow line
V1, V2 tube clamp
V3 electromagnetic valve

The invention claimed is:

1. A blood purification apparatus that includes
a blood circuit including an arterial blood circuit and a venous blood circuit and having a flow route that allows a patient's blood to extracorporeally circulate from a distal end of the arterial blood circuit to a distal end of the venous blood circuit;
a blood purifier connected to a proximal end of the arterial blood circuit and to a proximal end of the venous blood circuit and that purifies the patient's blood flowing through the blood circuit;
an air-trap chamber connected to the blood circuit and that traps bubbles contained in liquid flowing in the flow route of the blood circuit; and
a blood pump provided to the arterial blood circuit and being capable of delivering the liquid within the blood circuit,
the blood purification apparatus comprising:
an upstream bubble-detecting unit attached to a position of the blood circuit on an upstream side with respect to the air-trap chamber and that detects bubbles contained in the liquid flowing in the blood circuit; and
a control unit that upon detection of any bubbles by the upstream bubble-detecting unit reduces a flow rate of the liquid flowing into the air-trap chamber by driving the blood pump at a lower speed than the blood pump was driven before the bubbles were detected;
wherein a distance between the upstream bubble-detecting unit and the air-trap chamber is set based on the flow rate of the blood circuit and an inside diameter of a tube forming the blood circuit.

2. The blood purification apparatus according to claim 1, further comprising a substitution pump capable of performing substitution or priming by introducing dialysate into the blood circuit, wherein the control unit reduces driving speeds of the blood pump and the substitution pump at the detection of any bubbles by the upstream bubble-detecting unit.

3. The blood purification apparatus according to claim 1, further comprising a narrowing unit provided at a position of the blood circuit between the air-trap chamber and the upstream bubble-detecting unit and that is capable of reducing the flow rate of the liquid by narrowing the flow route of the blood circuit, wherein the control unit reduces, at the detection of any bubbles by the upstream bubble-detecting unit, the flow rate of the liquid flowing into the air-trap chamber by activating the narrowing unit to narrow the flow route.

4. The blood purification apparatus according to claim 1, wherein the control unit resets the flow rate of the liquid flowing into the air-trap chamber to a preset flow rate at an elapse of a predetermined time period after reducing the flow rate of the liquid.

5. A method of trapping bubbles in a blood purification apparatus, the apparatus including
a blood circuit including an arterial blood circuit and a venous blood circuit and having a flow route that allows a patient's blood to extracorporeally circulate from a distal end of the arterial blood circuit to a distal end of the venous blood circuit;
a blood purifier connected to a proximal end of the arterial blood circuit and to a proximal end of the venous blood circuit and that purifies the patient's blood flowing through the blood circuit;
an air-trap chamber connected to the blood circuit and that traps bubbles contained in liquid flowing in the flow route of the blood circuit;
a blood pump provided to the arterial blood circuit and being capable of delivering the liquid within the blood circuit, and
an upstream bubble-detecting unit attached to a position of the blood circuit on an upstream side with respect to the air-trap chamber;
wherein the method comprises:
detecting bubbles contained in the liquid flowing in the blood circuit,
reducing a flow rate of the liquid flowing into the air-trap chamber at the detection of any bubbles by an upstream bubble-detecting unit,
lowering a driving speed of the blood pump when the bubbles are detected by the upstream bubble-detecting unit; and
setting a distance between the upstream bubble-detecting unit and the air-trap chamber is set based on the flow rate of the blood circuit and an inside diameter of a tube forming the blood circuit.

6. The method of trapping bubbles in the blood purification apparatus according to claim 5, wherein the blood purification apparatus further includes a substitution pump capable of performing substitution or priming by introducing dialysate into the blood circuit, and reducing driving speeds of the blood pump and the substitution pump at the detection of any bubbles by the upstream bubble-detecting unit.

7. The method of trapping bubbles in the blood purification apparatus according to claim 5, wherein the blood purification apparatus further includes a narrowing unit provided at a position of the blood circuit between the air-trap chamber and the upstream bubble-detecting unit and that is capable of reducing the flow rate of the liquid by narrowing the flow route of the blood circuit; and, at the detection of any bubbles by the upstream bubble-detecting unit, the flow rate of the liquid flowing into the air-trap chamber is reduced by activating the narrowing unit to narrow the flow route.

8. The method of trapping bubbles in the blood purification apparatus according to claim 5, wherein the flow rate of the liquid flowing into the air-trap chamber is reset to a preset flow rate at an elapse of a predetermined time period after the flow rate of the liquid is reduced.

9. The method of trapping bubbles in the blood purification apparatus according to claim 5, wherein the flow rate of the liquid flowing into the air-trap chamber is reset to a preset flow rate at an elapse of a predetermined time period after the flow rate of the liquid is reduced.

10. The method of trapping bubbles in the blood purification apparatus according to claim 6, further comprising:
resetting the flow rate of the liquid flowing into the air-trap chamber to a preset flow rate at an elapse of a predetermined time period after the flow rate of the liquid is reduced.

11. The method of trapping bubbles in the blood purification apparatus according to claim 7, further comprising:
resetting the flow rate of the liquid flowing into the air-trap chamber to a preset flow rate at an elapse of a predetermined time period after the flow rate of the liquid is reduced.

12. The blood purification apparatus according to claim 1, wherein the control unit resets the flow rate of the liquid flowing into the air-trap chamber to a preset flow rate at an elapse of a predetermined time period after reducing the flow rate of the liquid.

13. The blood purification apparatus according to claim 2, wherein the control unit resets the flow rate of the liquid flowing into the air-trap chamber to a preset flow rate at an elapse of a predetermined time period after reducing the flow rate of the liquid.

14. The blood purification apparatus according to claim 3, wherein the control unit resets the flow rate of the liquid flowing into the air-trap chamber to a preset flow rate at an elapse of a predetermined time period after reducing the flow rate of the liquid.

\* \* \* \* \*